United States Patent [19]

Reid

[11] 4,427,420
[45] Jan. 24, 1984

[54] PUMPING METHOD AND APPARATUS

[76] Inventor: Laurance S. Reid, 601 Broad La., Norman, Okla. 73069

[21] Appl. No.: 414,631

[22] Filed: Sep. 3, 1982

[51] Int. Cl.$^3$ .............................................. B01D 53/14
[52] U.S. Cl. ........................................ 55/18; 55/20; 55/32; 55/160; 55/217; 55/225; 55/227; 55/228; 203/1; 203/3; 203/18
[58] Field of Search .................. 55/18, 20, 32, 33, 34, 55/160, 210, 217, 218, 219, 220, 225, 227, 228, 233; 203/1, 3, 18; 585/833, 834, 860

[56] References Cited

U.S. PATENT DOCUMENTS

| | | | |
|---|---|---|---|
| 2,990,910 | 7/1961 | Kimmell | 55/32 |
| 3,119,674 | 1/1964 | Glasgow | 55/20 |
| 3,333,398 | 8/1967 | Schneider | 55/18 |
| 3,451,897 | 6/1969 | Welch | 55/20 |
| 3,589,984 | 6/1971 | Reid | 203/18 |

Primary Examiner—Ernest G. Therkorn
Attorney, Agent, or Firm—Mason, Kolehmainen, Rathburn & Wyss

[57] ABSTRACT

The present invention makes use of spent or loaded process liquid at relatively high pressure to power a pump for recirculation of regenerated process liquid for gas contact in a relatively high pressure gas-liquid contact apparatus. In this manner, the power fluid used for recirculation supplies about 65% of the pumping energy requirements and the remaining 35% of the needed pumping energy is supplied by an externally powered pump, such as an electric motor-driven or engine powered pump. In accordance with the present invention, the power end of the fluid-power pump is flooded with liquid at all times so that no free gas is used. The extra volume of liquid used for pumping is regenerated and pumped back to the contactor by an externally powered pump, for example, a plunger-type, electrically-driven or engine-driven pump. The fluid-powered pump and plunger pump can be controlled to pump at a rate proportional to gas flow rate into or out of the contact apparatus or controlled to provide a predetermined amount of a particular gas component, i.e., water vapor content, in the gas leaving the gas-liquid contacting apparatus. Significant pumping energy and fuel savings result from employing substantially all liquid as the fluid to power the fluid-powered pump and in using a separate recirculation control means not directly related to liquid level within the contact apparatus.

12 Claims, 1 Drawing Figure

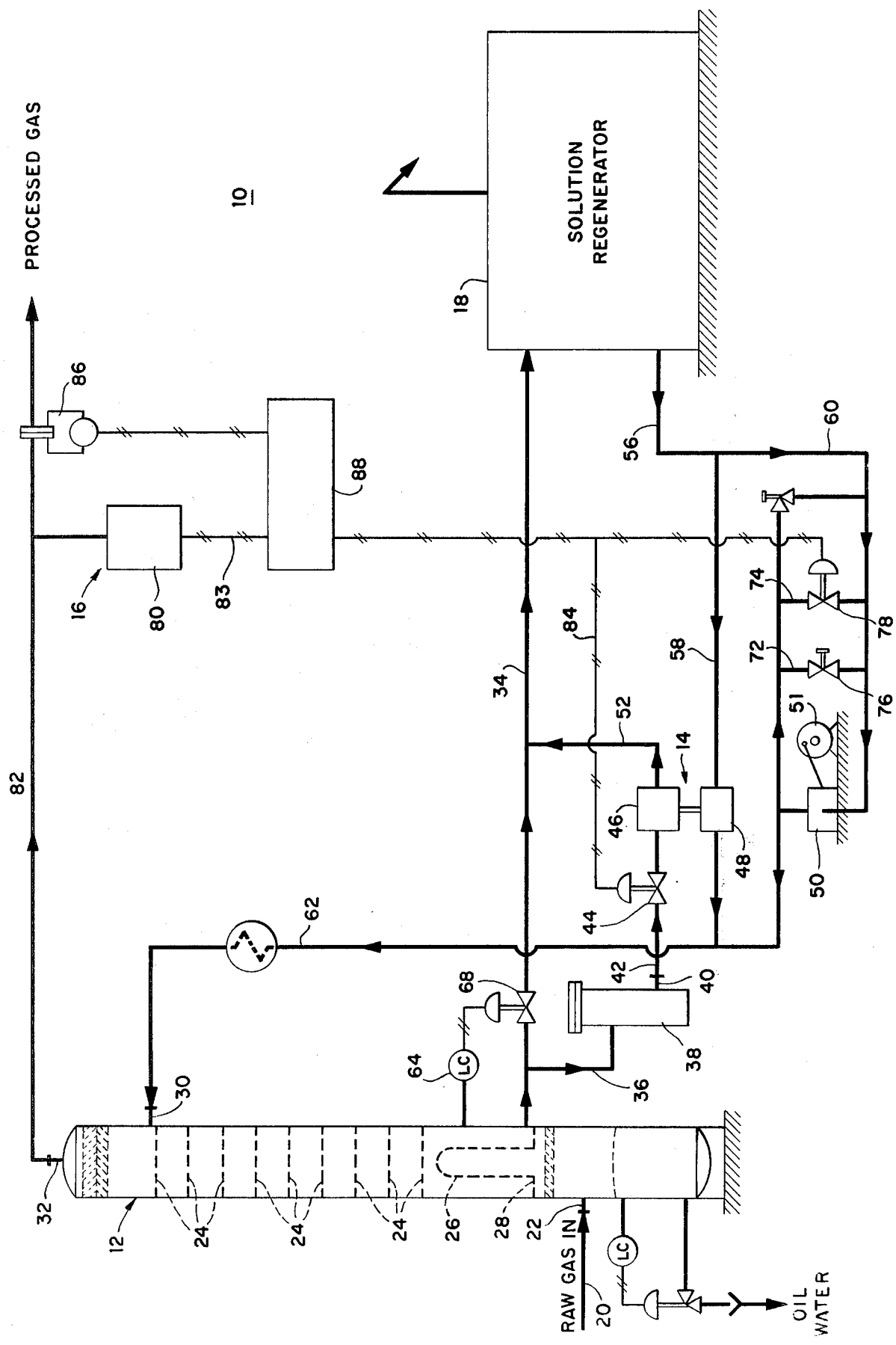

PUMPING METHOD AND APPARATUS

FIELD OF THE INVENTION

The present invention relates to an improved method and apparatus for pumping process absorbents or reactants to a gas-liquid contact apparatus in any gas-liquid process system involving mass transfer or reaction. More particularly, the present invention relates to an improved method and apparatus for pumping liquid process absorbents or reactants to a gas-liquid contact apparatus at a rate proportional to the gas flow rate into or out of the gas-liquid contact apparatus or at a rate sufficient to provide a predetermined content of a particular component in the processed gas leaving the gas-liquid contact apparatus.

BACKGROUND OF THE INVENTION AND PRIOR ART

Gas-liquid contacting apparatus is used in many industries, such as the natural gas industry, for removing desirable or undesirable constituents from gas mixtures. One common use for gas-liquid contacting apparatus is in removal of water vapor from gas, such as natural gas, by intimately contacting the natural gas with a liquid desiccant. Gas-liquid contacting apparatus also is commonly used in aminetype sour gas treaters, absorption-type hydrocarbon liquid recovery plants, and other processes.

In many larger systems, pumping energy for liquid recirculation is supplied from an outside source, such as an engine or electric motor, but in smaller systems, particularly those located remotely in the field, pumping energy is obtained solely from high pressure gas, before or after treatment, as disclosed in Kimmell U.S. Pat. No. 2,990,910.

In Kimmell U.S. Pat. No. 2,990,910, a pumping method and apparatus is disclosed wherein a pump is powered by a combination of liquid and gas from a gas-liquid contact apparatus, such as an absorber, and the pressure of the gas and liquids supplied to the pump is proportional to the amount of gas supplied to the power side of the pump. In this manner, when more gas pressure is supplied to the absorber, more power is supplied to the pump for recirculation of liquid for contact in the absorber. The fluids used to power a Kimray pump comprises two volumes of liquid plus one volume of gas which pumps back to the absorber two volumes of regenerated absorbent. The one volume of power gas is of doubtful quality for use as fuel and, particularly at system pressures greater than 300 psig, the quantity of power gas greatly exceeds the fuel requirement. In these instances, most of that gas is flared or vented to atmosphere, constituting a substantial waste of gas.

In accordance with the present invention, this gas waste has been entirely eliminated by using substantially only liquid to power the liquid recirculation pump and by controlling the rate of liquid recirculation to the gas-liquid contacting apparatus in a manner not directly responsive to the liquid level within the gas-liquid contact apparatus.

SUMMARY OF THE INVENTION

In brief, the present invention makes use of spent or loaded process liquid at relatively high pressure to power a pump for recirculation of regenerated process liquid for gas contact in a relatively high pressure gas-liquid contact apparatus. In this manner, the power fluid used for recirculation supplies about 65% of the pumping energy requirements and the remaining 35% of the needed pumping energy is supplied by an externally powered pump, such as an electric motor-driven or engine powered pump.

In accordance with the present invention, a fluid-powered pump, such as that shown in the Kimmell U.S. Pat. No. 2,990,910, is used to pump process liquid, after regeneration, back to a gas-liquid contacting apparatus for intimate contact with a rising gas stream.

In a pump such as that shown in the Kimmell U.S. Pat. No. 2,990,910, the volumetric ratio of power cylinder to pump cylinder is approximately 3:2 so that, in normal operation, the power cylinder employs 2 volumes of loaded process liquid, for example slightly-diluted glycol, and one volume of gas at the contact apparatus pressure to pump back to the contact apparatus two volumes of regenerated liquid, for example, reconcentrated glycol or other desiccant. In accordance with the present invention, the power end of the fluid-power pump is flooded with liquid at all times so that no free gas is used. The extra volume of liquid used for pumping is regenerated and pumped back to the contactor by an externally powered pump, for example, a plunger-type, electrically-driven or engine-driven pump. The fluid-powered pump and plunger pump can be controlled to pump at a rate proportional to gas flow rate into or out of the contact apparatus or controlled to provide a predetermined amount of a particular gas component, i.e., water vapor content, in the gas leaving the gas-liquid contacting apparatus. Significant pumping energy and fuel savings result from employing substantially all liquid as the fluid to power the fluid-powered pump and in using a separate recirculation control means not directly related to liquid level within the contact apparatus.

Accordingly, an object of the present invention is to provide a new and improved method of and apparatus for pumping liquid into a gas-liquid contact vessel utilizing dilute liquid collected in the contact vessel to provide the energy requirements of a fluid-powered pump without wasting gas from said contact vessel for fluid-powered pump energy.

Another object of the present invention is to provide a new and improved method of and apparatus for continuous gas-liquid mass transfer or reaction wherein a majority of the pumping power for pumping regenerated liquid to a gas-liquid contact vessel is provided by loaded or reacted liquid collected from the contact vessel and directed into a power cylinder of a fluid-powered pump to flood the power cylinder with liquid, and a smaller portion of the pumping power for pumping reconstituted liquid to the contact vessel is provided by an externally powered pump.

Another object of the present invention is to provide a new and improved method of and apparatus for continuous mass transfer or reaction in a gas-liquid contact vessel wherein the amount of liquid pumped into the contact vessel for mass transfer or reaction with the gas is determined by, and controlled in response to, a predetermined amount of key component measured in the treated or processed gas exiting the contact vessel.

Still another object of the present invention is to provide a new and improved method of and apparatus for continuous mass transfer or reaction between a gas and a liquid in a gas-liquid contact vessel where the flow rate of liquid pumped into the contact vessel is determined by, and controlled in response to, the flow rate of processed gas leaving the contact vessel.

BRIEF DESCRIPTION OF THE DRAWING

These and other objects and advantages of the present invention will be apparent from the following detailed description of the invention described with reference to the drawing showing a schematic flow diagram of the method and apparatus of the present invention.

DETAILED DESCRIPTION

Referring now to the drawing there is illustrated a new and improved apparatus for pumping process absorbents or reactants through a gas-liquid contact apparatus in any process system utilizing mass transfer or reaction in a gas-liquid contact apparatus. The apparatus of the drawing, generally designated by reference numeral 10, generally includes a gas-liquid contact apparatus or absorber 12; a fluid-powered pump, generally designated by reference numeral 14, a control device, generally designated by reference numeral 16 for controlling the amount of liquid recirculated to the gas-liquid contact apparatus 12; and a solution regenerator 18 for regenerating spent or dilute liquid collected at the bottom of gas-liquid contact apparatus 12 to make the liquid suitable for recirculation to the top of the gas-liquid contact apparatus 12 for additional mass transfer or reaction with the entering gas. For purposes of illustration, the method and apparatus of the present invention will be described as applied to the removal of water from natural gas at relatively high pressure, i.e., 300 to 3000 psig.

Referring now to FIG. 1, raw or wet natural gas is conveyed from a gas well (not shown) through conduit 20 into a feed gas-inlet 22 disposed in a lower portion of gas-liquid contact apparatus or absorber 12. Absorber 12 is a typical gas-liquid contact apparatus having a plurality of trays 24 or may be a column packed with Raschig rings, bubble cap trays or any apparatus suitable for providing intimate contact between rising gas and descending liquid. The lowermost tray in the absorber 12 is a chimney tray 28 capable of maintaining a predetermined liquid level above its base so that loaded or reacted liquid collected around the chimney 26 may be regenerated and recirculated to a liquid inlet 30 of absorber 12 as will hereinafter be described in more detail.

In the absorber 12, a liquid desiccant such as glycol enters the absorber 12 through liquid inlet 30 and descends in intimate contact with the relatively high pressure, i.e., 300 to 3000 psig, natural gas rising in the absorber 12 via gas inlet 22 so that water from the natural gas is absorbed in the desiccant and the water-laden or loaded desiccant is collected above the base of chimney tray 28. Dried natural gas leaves the absorber 12 at processed gas outlet 32.

Liquid collected on chimney tray 28 leaves the absorber through conduit 34 and this water-laden or dilute glycol is directed through conduit 36 into filter 38 where substantially all abrasives are removed from the dilute glycol. The filtered, dilute glycol exits the filter 38 at filter outlet 40 and passes through conduit 42 and flow control valve 44 to a power cylinder 46 of the fluid-powered pump 14 where the dilute glycol, in the form of substantially 100% liquid, provides approximately ⅔ or about 65% of the energy requirements necessary to recirculate regenerated glycol through a pump cylinder 48 of the fluid-powered pump 14. Since the volumetric ratio of the power cylinder 46 to the pump cylinder 48 is approximately 3:2, approximately 3 volumes of dilute glycol through the power cylinder 46 will be needed to pump approximately 2 volumes of regenerated glycol through the pump cylinder 48 to the absorber 12. Accordingly, since only liquid is flowing through the power cylinder 46, an externally powered, i.e., electrical or engine-driven pump 50 is required to recirculate the other ⅓ of the regenerated glycol back to the absorber inlet 30. Externally powered pump 50 is powered by an electrical or motor source of energy shown diagrammatically by reference numeral 51.

The dilute glycol used to power the fluid-powered pump 14 exits the power cylinder 46 through conduit 52 and passes through conduit 34 into the solution regenerator 18. Solution regenerator 18 may be any apparatus useful in removing from the liquid any undesirable contaminant absorbed by or removed by mass transfer or reaction with the gas entering the absorber 12. For purposes of the illustrated embodiment, solution regenerator 18 is any apparatus capable of removing water from the dilute liquid desiccant, for example, the apparatus disclosed in my prior U.S. Pat. No. 3,589,984 or a flash tank as disclosed in Kimmell U.S. Pat. No. 2,990,910, to restore the desiccant to less than about 1.0% water, and in all cases to increase the desiccant concentration. Preferably, the solution regenerator 18 is a COLDFINGER unit as disclosed in my prior U.S. Pat. No. 3,589,984. The regenerated desiccant exits solution regenerator 18 through conduit 56 and approximately ⅔ of the regenerated desiccant flows through conduit 58 to the pump cylinder 48 of the fluid-powered pump 14 and approximately ⅓ of the regenerated desiccant flows through conduit 60 to the externally powered pump 50 to pump the regenerated desiccant through conduit 62 into the liquid inlet 30 of the absorber 12.

A level controller 64 is disposed a predetermined distance above the base of chimney tray 28 to actuate a motor valve 68 disposed in dilute glycol pump feed conduit 34 to prevent the dilute glycol from rising above the top of chimney 26. In the event of erratic feed of regenerated glycol to contactor 12 through conduit 62, the level on the chimney tray 28 may rise. In that event, the level controller 64 will actuate the motor valve 68 to release excess dilute glycol to the solution regenerator 18 through conduit 34. Additionally, the dilute glycol pump feed conduit 34 is disposed a predetermined distance above the base of chimney tray 28 to provide substantially 100% liquid flowing through conduit 36, filter 38 and conduit 42 into the power cylinder 46 of the fluid-powered pump 14. If the liquid level above the base of chimney tray 28 drops below the level of dilute glycol pump feed conduit 34, some gas will enter the power cylinder 46 of fluid-powered pump 14 to drive the fluid-powered pump 14 until the liquid level above the base of chimney tray 28 rises again above the dilute glycol exit conduit 34.

Conduits 72 and 74 are provided in fluid communication with the externally powered pump 50 to provide a recirculation loop around the externally powered pump 50. One circulation loop is capable of being controlled manually by valve 76 and another recirculation loop is capable of being controlled automatically by control valve 78. The pumping capacity of the electric pump 50 can be adjusted manually by setting by-pass valve 76 to permit excess regenerated glycol to by-pass recirculation line 62 and absorber inlet 30 when there is less regenerated glycol in the pump cylinder 48 of the fluid-powered pump 14 as a result of less dilute desiccant passing through the power cylinder 46 of the fluid-powered pump 14.

In accordance with an important feature of the present invention, considerable economy is achieved by the control device 16 to provide a controlled amount of dilute glycol feed to the power cylinder 46 of the fluid-powered pump 14. Control instrumentation is available for monitoring the water vapor content in flowing gas streams to generate signals proportional to the water vapor content for actuating electronic controls. Similarly, an ethanolamine or other liquid reagent system for treating sour gas would pump regenerated liquid through the power cylinder 46 of the fluid-powered pump 14 to a predetermined level of analyzed $H_2S$ and/or $CO_2$ in the processed gas using any one of many available signal-generating control systems to monitor the $H_2S$ and/or $CO_2$ in the processed gas stream, as shown in FIG. 1.

In accordance with the present invention, the control device 16 includes a processed gas analyzer 80 capable of detecting the water vapor content of the processed gas in processed gas conduit 82. A typical control device is manufactured by Panametrics, Hygrometer Systems I or II. An electronic signal determined by the water vapor content in the processed gas is sent by electrical connections 83 and 84 to control valves 44 and 78 thereby controlling the dilute glycol feed to the power cylinder 46 of fluid-powered pump 14 to control the amount of regenerated or reconcentrated glycol by-passing the electrical or externally powered pump 50 in recirculating regenerated glycol. In this manner, more regenerated glycol is circulated to the absorber when the water vapor content of the processed gas is too high and less regenerated glycol is recirculated when the water vapor content of the processed gas is lower than required.

In accordance with an important embodiment of the present invention the control system circulates treating liquids at a rate which will produce an essentially constant level of the key component, i.e., water vapor, in the effluent or processed gas stream. Since gas throughputs can vary widely within a short interval, fluctuations which are so characteristic of gas producing operations, this feature saves significant quantities of fuel gas while, at the same time, it compensates for deficiencies in mass and heat transfer caused by large turndowns, or low flow rates. The signal-generating gas analyzer 80 monitors the concentration of at least one key component in the effluent or processed gas and its signal energizes a control panel 88 which, in turn, actuates control valves 44 and 78, either electronically and/or pneumatically, the latter via an electronic-pneumatic interface in panel 88.

In accordance with another embodiment of the control device 16 of the present invention, a proportioning flow meter 86 is disposed in the processed gas conduit 82 to control the pumping rate of both the fluid-powered pump 14 and the electrical pump 50 in proportion to the amount of gas flowing through the processed gas line 82. A typical flow meter control device is manufactured by ITT Barton Model No. 335.

Referring more particularly to the alternate control system utilizing the proportioning flow meter 86, the proportional controller 86 generates a signal to energize valves 44 and 78 to cause the fluid-powered pump 14 and the electrical pump 50 to circulate treating liquid in precise, direct proportion to gas flow rate. This, too, will save substantial amounts of fuel, but key component, i.e., water vapor quality in the effluent gas will vary with flow rate because of variations in heat and mass transfer rates caused by flow rate variations.

What is claimed and desired to be secured by Letters Patent of the United States is:

1. Apparatus for continuous gas-liquid mass transfer or reaction comprising:
    a gas-liquid contact means for causing intimate contact between a gas and a liquid under pressure for causing mass transfer or reaction between said gas and said liquid to form a dilute or reacted liquid and a processed gas exiting said contact means;
    regenerator means at a pressure lower than said pressure in said gas-liquid contact means for regenerating said dilute or reacted liquid to form a regenerated liquid;
    means for supplying gas to said contact means under pressure;
    a fluid-powered pump in fluid communication with said treating vessel means and in fluid communication with said gas-liquid contact means for pumping a portion of said regenerated liquid from said treatment vessel means to said gas-liquid contact means;
    an externally-powered pump for pumping a portion of said regenerated liquid from said regenerating means to said gas-liquid contact means to maintain system balance; and
    means for supplying substantially only dilute liquid from said gas-liquid contact means to a power cylinder portion of said fluid-powered pump maintained flooded with liquid to provide pumping energy to said fluid-powered pump.

2. The apparatus of claim 1 including means operatively connected to a control means for measuring the concentration of a key component in said processed gas; and
    means for controlling the flow of feed of said dilute liquid from said gas-liquid contact means to said fluid-powered pump, in response to said concentration of said key component in said processed gas.

3. The apparatus of claim 2 including means for controlling the flow of feed of regenerated liquid from said externally powered pump to said gas liquid contact means in response to said concentration of said key component in said processed gas.

4. The apparatus of claim 1 including a by-pass conduit loop having a valve therein for controlled recirculation of reconcentrated liquid by said externally powered pump through said by-pass loop, so that the flow of regenerated liquid pumped to said gas-liquid contact means by said externally powered pump is proportional to the flow of reconcentrated liquid pumped to said gas-liquid contact means by said fluid-powered pump.

5. The apparatus of claim 1 including a by-pass conduit in fluid communication between said gas-liquid contact means and said regeneration means for directing a portion of said dilute liquid from said gas-liquid contact means to said regeneration means without passing said dilute liquid portion through said power cylinder of said fluid-powered pump.

6. A method of continuous gas-liquid mass transfer or reaction comprising:
    directing a feed gas, under pressure, into a lower portion of a gas-liquid contact device and directing a liquid, under pressure, into an upper portion of said contact device to cause intimate contact and mass transfer or reaction between said gas and liquid within said contact device and to form a dilute or reacted liquid and a processed gas, under pressure, collected from said contact device;

directing at least a portion of said dilute liquid, under pressure, from said contact device into the power cylinder of a fluid-powered pump to substantially completely flood said power cylinder with dilute liquid;

directing said dilute liquid from an exit of said power cylinder into a regeneration means, said regeneration means being at a pressure lower than the pressure of said contact device;

treating said dilute liquid in said regeneration means to regenerate said dilute liquid to a degree sufficient to achieve additional mass transfer or reaction with feed gas in said contact device;

pumping a portion of said regenerated liquid from said regeneration means to said contact device through a pump cylinder of said fluid-powered pump; and pumping another portion of said regenerated liquid from said regeneration means to said contact device with an externally-powered pump.

7. The method of claim 6 including measuring the concentration of a key component in said processed gas and controlling the flow of said dilute liquid directed from said contact means into said power cylinder of said fluid powered pump in response to the measured concentration of said key component in said processed gas.

8. The method of claim 7 including controlling the flow of regenerated liquid pumped through the externally-powered pump to said contact device in response to said concentration of said key component in said processed gas.

9. The method of claim 6 including recirculating a portion of said regenerated liquid from said regeneration means through a recirculation loop by said externally powered pump so that said recirculated, regenerated liquid portion does not enter said contact device during recirculation.

10. The method of claim 9 wherein the flow of said recirculated regenerated liquid is determined by the flow of regenerated liquid pumped to said contact device by said fluid-powered pump.

11. The method of claim 10 wherein the amount of regenerated liquid pumped to the contact device by said externally powered pump is proportional to the flow of regenerated liquid pumped to said contact device by said fluid-powered pump.

12. The method as defined in claim 6 including directing a portion of said dilute liquid from said contact device to said regeneration means without said dilute liquid portion passing through the power cylinder of said fluid-powered pump.

* * * * *